(12) United States Patent
Kiss et al.

(10) Patent No.: US 6,787,576 B2
(45) Date of Patent: Sep. 7, 2004

(54) LINEAR ALPHA OLEFINS FROM NATURAL GAS-DERIVED SYNTHESIS GAS OVER A NONSHIFTING COBALT CATALYST

(75) Inventors: Gabor Kiss, Hampton, NJ (US); Rocco Anthony Fiato, Basking Ridge, NJ (US); Frank Hershkowitz, Liberty Corner, NJ (US); David Chester Long, Ashburn, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/330,860

(22) Filed: Dec. 27, 2002

(65) Prior Publication Data

US 2004/0127582 A1 Jul. 1, 2004

(51) Int. Cl.[7] .............................................. C07C 27/00
(52) U.S. Cl. ...................... 518/715; 518/700; 518/706; 518/708; 518/712
(58) Field of Search ................................ 518/700, 706, 518/708, 712, 715

(56) References Cited

U.S. PATENT DOCUMENTS

| | | | |
|---|---|---|---|
| 4,048,250 A | 9/1977 | Garwood et al. | 260/683.43 |
| 4,279,830 A | 7/1981 | Haag et al. | 518/700 |
| 4,532,229 A | 7/1985 | Fiato et al. | 502/330 |
| 4,542,117 A | 9/1985 | Morris et al. | 502/66 |
| 4,544,674 A | 10/1985 | Fiato et al. | 518/717 |
| 4,579,986 A | 4/1986 | Sie | 585/324 |
| 4,584,323 A | 4/1986 | Soled et al. | 518/700 |
| 4,585,799 A | 4/1986 | Morris et al. | 518/717 |
| 4,594,172 A | 6/1986 | Sie | 252/55 |
| 4,639,431 A | 1/1987 | Gates et al. | 502/304 |
| 5,100,856 A | 3/1992 | Soled et al. | 502/329 |
| 5,118,715 A | 6/1992 | Iglesia et al. | 518/713 |
| 5,210,060 A | 5/1993 | Radlowski et al. | 502/202 |
| 5,248,701 A | 9/1993 | Soled et al. | 518/700 |
| 6,166,262 A | 12/2000 | Connor | 568/460 |

FOREIGN PATENT DOCUMENTS

| | | | |
|---|---|---|---|
| GB | 2169614 A | 7/1986 | C07C/1/04 |
| JP | 61018433 A | 1/1986 | B01J/21/16 |
| NL | 7712952 A | 5/1979 | B01J/23/74 |

OTHER PUBLICATIONS

R. Madon et al., "Primary and Secondary Reaction Pathways in Ruthenium–Catalyzed Hydrocarbon Synthesis", *The Journal of Physical Chemistry*, 1991, 95, pp. 7795–7804.

E. Iglesia et al., "Transport–Enhanced α–Olefin Readsorption Pathways in Ru–Catalyzed Hydrocarbon Synthesis", *Journal of Catalysis*, vol. 129, pp. 238–256 (1991).

R. J. Madon et al., "Non–Flory Product Distributions in Fischer–Tropsch Synthesis Catalyzed by Ruthenium, Cobalt, and Iron", ACS Symposium Series Selectivity in Catalysis, Editors: M. E. Davis and S. L. Suib, New York, Aug. 25–30, 1991.

E. Igesia et al., "Selectivity Control and Catalyst Design in the Fischer–Tropsch Synthesis: Sites, Pellets and Reactors", *Advances in Catalysis*, vol. 39, 1993, pp. 221–302.

(List continued on next page.)

*Primary Examiner*—J. Parsa
(74) *Attorney, Agent, or Firm*—Estelle C. Bakun

(57) ABSTRACT

Linear alpha olefins having from four to twenty carbon atoms and low amounts of oxygenates are synthesized, by producing a synthesis gas containing $H_2$ and CO from natural gas and passing it over a non-shifting cobalt catalyst at reaction conditions of temperature, % CO conversion, and gas feed $H_2$:CO mole ratio land water vapor pressure, effective for the mathematical expression $200-0.6T+ 0.03P_{H2O}-0.6X_{CO}-8(H_2:CO)$ to have a numerical value greater than or equal to 50. This process can be integrated into a conventional Fischer-Tropsch hydrocarbon synthesis process producing fuels and lubricant oils.

20 Claims, 2 Drawing Sheets

OTHER PUBLICATIONS

H. Schulz et al., "Effect of Water Partial Pressure on Steady State Fischer–Tropsch Activity and Selectivity of a Promoted Cobalt Catalyst", 4th International Natural Gas Conversion Symposium (Kruger Park, South Africa Nov. 19–23, 1995) *Studies in Surface Science and Catalysis* V107, pp. 193–200 (1997).

E. Iglesia, "Fischer–Tropsch Synthesis on Cobalt Catalysts: Structural Requirements and Reaction Pathways", 4th International Natural Gas Conversion Symposium (Kruger Park, South Africa Nov. 19–23, 1995) *Studies in Surface Science and Catalysis* V107, pp. 153–162 (1997).

E. Iglesia et al., "Dispersion, Support, and Bimetallic Effects in Fischer–Tropsch Synthesis on Cobalt Catalysts", 3rd National Gas Conversion Symposium (Sydney, Australia Jul. 4–9, 1993) Studies in Surface Science and Catalysis, V81, pp. 433–442 (1994).

E. Iglesia et al., "Bimetallic Synergy in Cobalt–Ruthenium Fischer–Tropsch Synthesis Catalysts", *Journal of Catalysis*, vol. 143, pp. 345–368 (1993).

E. Iglesia et al., "Fischer–Tropsch Synthesis on Cobalt and Ruthenium. Metal Dispersion and Support Effects on Reaction Rate and Selectivity", *Journal of Catalysis*, vol. 137, No. 1 Sep. 1992.

R. Snell, "Olefins from Syngas", Catal. Rev. Sci. Eng., 29(4), pp. 361–445 (1987).

E. Iglesia, "Selectivity Control, Catalysts, and Reactors in the Fischer–Tropsch Synthesis", based on a lecture delivered at the 1997 Spring Meeting of the American Institute of Chemical Engineers, Houston, TX, Mar. 12, 1997.

S. Soled et al., "Activity and Selectivity Control in Iron Catalyzed Fischer–Tropsch Synthesis", *Catalysis Letters* 7 (1990), pp. 271–280.

E. Iglesia, "Computer–Aided Design of Catalysts", edited by E.R. Becker and C.J. Pereira, Marcel Dekker, Inc., New York, 1993.

T. Riedel et al., "Fuels and Petrochemicals from CO2 Via Fischer–Tropsch Synthesis—Steady State Catalyst Activity and Selectivity", *Advances in Chemical Conversions for Mitigating Carbon Dioxide Studies in Surface Science and Catalysis*, vol. 114, 1998.

A.M. Humen et al., "Fischer–Tropsch Synthesis on Supported Cobalt Catalysts Promoted by Noble Metals", ACS 207th National Meeting (San Diego Mar. 13–17, 1994)—abstract.

LINEAR ALPHA OLEFINS FROM NATURAL GAS-DERIVED SYNTHESIS GAS OVER A NONSHIFTING COBALT CATALYST

BACKGROUND OF THE DISCLOSURE

1. Field of the Invention

The invention relates to producing linear alpha olefins from synthesis gas over a cobalt catalyst. More particularly the invention relates to producing $C_4$–$C_{20}$ linear alpha olefins having low amounts of oxygenates, by reacting $H_2$ and CO in a synthesis gas produced from natural gas, over a non-shifting cobalt catalyst at reaction conditions of temperature, % CO conversion, $H_2$:CO mole ratio and water vapor pressure effective for the mathematical expression of $200-0.6T+0.03P_{H2O}-0.6X_{CO}-8(H_2:CO)$ to have a numerical value greater than or equal to 50. This can be integrated into a Fischer-Tropsch hydrocarbon synthesis process producing fuels and lubricant oils.

2. Background of the Invention

Linear alpha olefins in the $C_4$–$C_{20}$ carbon atom range are large volume raw materials used in the production of, for example, polymers, detergents, lubricants and PVC plasticizers. The demand for these olefins is rapidly increasing, particularly for those that have from 6 to 12 carbon atoms, such as six and eight carbon atom linear alpha olefins desirable for making polyolefin plastics Most linear alpha olefins are produced by ethene oligomerization, for which the ethene feed cost can account for more than half the total cost of the alpha olefin production. It is known that alpha olefins can be produced from synthesis gas using iron, iron-cobalt, iron-cobalt spinel, copper-promoted cobalt and cobalt manganese spinel catalysts, most of which are shifting catalysts. Examples of linear alpha olefin production with such catalysts may be found, for example, in U.S. Pat. Nos. 4,544,674; 5,100,856; 5,118,715; 5,248,701; and 6,479,557. U.S. Pat. No. 6,479,557, for example, discloses a two-stage process to make paraffinic hydrocarbons in the first stage and olefinic hydrocarbons in the second stage. The paraffinic product is made by converting a substoichiometric synthesis gas feed (i.e., $H_2$/CO feed ratio lower than about 2.1:1) over a non-shining catalyst in the first stage. Since the $H_2$/CO usage ratio is stoichiometric, the effluent of the first stage is significantly depleted in CO. This effluent of the first stage is then used to make olefinic hydrocarbons in the second stage over a shifting Fischer-Tropsch catalyst.

Although iron-based shifting catalysts produce hydrocarbons from synthesis gas with high alpha olefin content even at high CO conversion levels, the undesirable water gas shift reaction associated with shifting catalysts wastes part (as much as 50%) of the CO feed by converting CO to $CO_2$. Furthermore, in addition to high CO loss due to the water gas shift conversion of CO to $CO_2$, iron-based catalysts produce linear alpha olefins containing more than 1 and even as much as 10 wt. % oxygenates. These oxygenates are poisons to catalysts used for producing polymers and lubricants from olefins. Hence, the concentration of oxygenates must be reduced to a level acceptable for polymer and lubricant production. The methods used for removing the oxygenates are costly, thus catalysts and processes yielding olefin products with low oxygenate content is highly desired.

It would be an improvement to the art if a way could be found to (i) produce linear alpha olefins with low oxygenates levels and particularly with (ii) non-shifting catalyst and preferably a non-shifting Fischer-Tropsch hydrocarbon synthesis catalyst that is also useful for synthesizing fuel and lubricant oil fractions. It would be a still further improvement if (a) linear alpha olefin production could be integrated into a Fischer-Tropsch hydrocarbon synthesis process and (b) if a hydrocarbon synthesis reactor employing a non-shifting Fischer-Tropsch hydrocarbon synthesis catalyst and producing fuel and lubricant oil fraction hydrocarbons could also be used for linear alpha olefin production, and vice-versa, without having to change the catalyst in the reactor.

SUMMARY OF THE INVENTION

The invention relates to a process for producing linear alpha olefins, and particularly linear alpha olefins having from four to twenty carbon atoms, having less than 3 and preferably less than 1 wt. % oxygenates, by reacting $H_2$ and CO, in the presence of a non-shifting Fischer-Tropsch hydrocarbon synthesis catalyst comprising a catalytic cobalt component, under reaction conditions defined by a Condition Factor (CF) greater than or equal to 50, which Condition Factor is defined as:

$$CF = 200 - 0.6T + 0.03P_{H2O} - 0.6X_{CO} - 8(H_2:CO)$$

where,

T=average reactor temperature in ° C.; the average reactor temperature is calculated by averaging the temperature readings from thermocouples measuring the temperatures of individual segments of the reactor. For example, if the temperature is measured in the middle of the first, second, and third equal-volume segments of a fixed bed reactor, the average temperature is equal to one third of the sum of the three readings.

$P_{H2O}$=partial pressure of the water in the synthesis gas feed to the reactor, in kPa; the partial pressure of water in the feed is calculated by multiplying the mol fraction of water in the feed by the feed pressure measured in kPa. The mol fraction of feed components can be determined by, for example, using gas chromatographic methods.

$X_{CO}$=CO conversion expressed as percent; the CO conversion can be determined from the CO balance. There are many methods available for establishing material balance. The method herein utilized measurements based on an internal standard such as a noble gas or nitrogen that is inert during Fischer-Tropsch synthesis. When using an inert internal standard, the conversion can be simply calculated by measuring the concentrations of CO and the internal standard in the feed and the effluent. This and other calculation methods are well known in the art of chemical engineering. The concentrations of CO and the inert internal standard in turn can be determined by gas chromatographic methods known in the art.

$H_2$:CO=$H_2$ to CO molar ratio in the synthesis gas feed to the reactor; the concentrations of $H_2$ and CO in the feed can be determined by gas chromatographic methods.

By nonshifting is meant that under the reaction conditions the catalyst will convert less than 5 and preferably less than 1 mole % of the CO to $CO_2$ up to 90% CO conversion in Fischer-Tropsch synthesis. The wt. % of oxygenates is meant the wt. % of oxygenates in the total synthesized $C_4$–$C_{20}$ hydrocarbon fraction, and by oxygenates is meant oxygen-containing hydrocarbon molecules, such as alcohols, aldehydes, acids, esters, ketones, and ethers. The process of the invention has been found to produce a $C_4$–$C_{20}$ hydrocarbon fraction containing more than 50 wt. % linear alpha olefins and less than 3 wt. % preferably less than 1 wt. % oxygenates. This process can be achieved as a stand-alone process or it can be added to or integrated into a Fischer-Tropsch hydrocarbon synthesis process. The relatively low selectivity for alpha olefin production normally exhibited by a non-shifting Fischer-Tropsch cobalt catalyst, is at least partially overcome by operating the hydrocarbon synthesis reactor under reaction conditions in which the CF, according to the above expression, is greater than or equal to 50. By CO conversion is meant the amount of CO in the synthesis gas feed converted in a single pass through the reactor.

In another embodiment the invention relates to (a) producing a CO and $H_2$ containing synthesis gas from natural gas, (b) reacting the $H_2$ and CO containing synthesis gas in the presence of a non-shifting cobalt Fischer-Tropsch hydrocarbon synthesis catalyst, at reaction conditions effective to achieve a Condition Factor (CF) greater than or equal to 50, to synthesize linear alpha olefins, and particularly linear alpha olefins having from four to twenty carbon atoms having less than 3 wt. %, preferably less than 1 wt. % oxygenates. A process in which natural gas is converted to synthesis gas which, in turn, is converted to hydrocarbons, is referred to as a gas conversion process. In yet another embodiment, the process of the invention relates to an integrated gas conversion process, in which the linear alpha olefin production process of the invention is integrated with a hydrocarbon synthesis process which produces primarily fuel and lubricating oil products. This is explained in detail below.

It is preferred in the practice of the invention that the synthesis gas be produced from natural gas. Natural gas typically comprises mostly methane, for which the H:C ratio is 4:1 and is therefore an ideal feed for producing synthesis gas having a nominal $H_2$:CO mole ratio of 2:1 or somewhat higher, for example 2.1:1. Substantial amounts of hydrogen can be separated from a synthesis gas with a $H_2$:CO=2:1 mole ratio, to produce $H_2$ and a 1:1 $H_2$:CO mole ratio synthesis gas. The 1:1 $H_2$:CO mole ratio is a preferred ratio for the linear alpha olefin process of the invention. Thus, while the synthesis gas produced in the synthesis gas generating reactor of a gas conversion plant typically has an $H_2$:CO mole ratio of 2.1:1 or 2:1, all or a portion of this synthesis gas may be optionally treated to change the $H_2$:CO mole ratio in the gas to a more preferred ratio for the alpha olefin synthesis process, before it is passed into the one or more linear alpha olefin producing reactors.

It is understood that although the chemistry involved in producing linear,alpha olefins over a non-shifting Fischer-Tropsch cobalt catalyst is such that it is preferred for the $H_2$:CO mole ratio in the synthesis gas feed passed into the linear alpha olefin reactor be typically less than 2:1, the stoichiometric $H_2$:CO consumption mole ratio of the linear alpha olefin reaction is 2:1. Furthermore, it is also understood that conventional hydrocarbon synthesis making paraffinic hydrocarbons for fuel and lubricant applications over a non-shifting cobalt catalyst employs a synthesis gas feed in which the $H_2$:CO mole ratio is 2.1:1. In an integrated gas conversion process of the invention, one or more reactors may be added to and/or switched back and forth from hydrocarbon synthesis for producing fuel and lubricant fractions to linear alpha olefin production by changing the conditions from the conventional hydrocarbon synthesis conditions to the alpha olefin selective conditions of the present invention by adjusting the reaction parameters to achieve a CF value of greater than or equal to 50 and vice versa. Thus, producing the synthesis gas from natural gas provides a particular synergy and flexibility for practicing all embodiments of the present invention.

A CF value of greater than or equal to 50 can be achieved by many different combinations of temperature, CO conversion, $H_2$:CO ratio and water partial pressure. The individual process conditions that are preferred for achieving CF greater than or equal to 50, and thus high alpha olefin selectivity and concomitant production, include (a) setting the $H_2$:CO ratio in the synthesis gas feed to a value less than 2.1:1 and preferably less than 1.8:1, (b) a CO feed conversion of less than 50 and preferably less than 30% in a single pass through the reactor, and (c) a reaction temperature typically between 160 and 250 and preferably between 180 and 240° C. The presence of water in the synthesis gas feed, while optional, is preferred. Thus, it is possible for the value for $P_{H2O}$ in the expression above to be zero or negligible but a non-zero value in the range of from 50 to 500 kPa is preferred.

It is understood that although the above-specified preferred ranges provide guidance for the typical values of the individual control variables, (i.e., average reactor temperature, partial pressure of water and $H_2$:CO ratio in the gas feed to the reactor, and CO conversion) under which a Condition Factor value of greater than or equal to 50 can be achieved, it is the combination of the control variables which satisfy the CF described herein which is the invention not the individual variables alone . Thus the skilled artisan should appreciate that the invention is a linear combination of the control variables as defined by the Condition Factor. The utility of the Condition Factor is that it enables the determination of this preferred combination of the control variables. Thus, for example, if for economic or process reasons the feed to the reactor does not have steam (i.e., $P_{H2O}$=0 kPa), and the CO conversion needs to be at least 30%, the $H_2$:CO ratio in the feed to the linear alpha olefin reactor and the average reactor temperature need to be set so that the sum of 0.6(T) and 8($H_2$:CO) is less than 200−18−50=132. If, again, for process reasons the temperature is set for 205° C., the $H_2$:CO ratio needs to be less than 1.125:1 for the process of the invention. Clearly, if three control variables are set for process or economic reasons, the preferred value range of the fourth variable can be readily calculated. Those skilled in the art will also recognize, that if only two control variables are fixed, the preferred combinations of the remaining two variables will define a two-dimensional surface which will be further defined by some other common boundary conditions known in the art, like that the $H_2$:CO ratio cannot be equal or less than zero (no hydrocarbons form in the absence of $H_2$) or that the reaction temperature cannot be below 160° C. (where for the catalyst systems of interest to the process of this invention, the Fischer Tropsch reaction rate is too low to be practical). Likewise, if only one control variable is fixed, the preferred conditions define a three-dimensional space. It is clear, therefore, that while the specific preferred ranges given earlier for the individual control variables provide reasonable starting points, the ultimate combination of the control variables of the invention need to be derived from the expression provided herein for the Condition Factor.

Thus, although Applicants have specified preferred ranges for the input variables for CF (T, $P_{H2O}$, $X_{CO}$ and $H_2$:CO) so long as the specified CF is met, the input variables may vary from the ranges specified herein. Hence the CF criteria disclosed herein, is the criteria which must be met when setting the noted input variables.

Lower CO conversion can be readily achieved by increased, synthesis gas feed rates through the reactor, which also results in shorter product residence times. As a consequence, synthesis gas feed rate is another variable that may be used to achieve the desired conversion level and thus a CF greater than or equal to 50. Thus, the synthesis gas feed rate (commonly quantified as Gas Hourly Space Velocity or GHSV) through the reactor, with a non-shifting catalyst such as disclosed in U.S. Pat. No. 5,945,459, U.S. Pat. No. 5,968,991, U.S. Pat. No. 6,090,742, U.S. Pat. No. 6,136,868, U.S. Pat. No. 6,319,960, RE 37,406, U.S. Pat. No. 6,355,593, U.S. Pat. No. 6,331,575 comprising a catalytic cobalt component, will typically be greater than 15,000 standard volumes of gas (measured at 103 kPa and 25° C.)/volume of catalyst/hour (V/V/hr), and preferably greater than 25,000 V/V/hr. It is understood, however, that the feed rate necessary to maintain the preferred CO conversion of the invention will also depend on the volumetric productivity of the catalyst. Hence, as would be readily apparent to the skilled artisan, a catalyst that has two times higher volumetric activity, will require two times faster feed rate to maintain the same CO conversion or 50,000 v/v/hr.

These conditions, particularly the low CO feed conversion and high synthesis feed gas rate through the reactor, are more readily achieved in a reactor containing one or more fixed beds of catalyst or a fluidized catalyst. A slurry reactor, highly efficient for synthesizing higher molecular weight paraffinic hydrocarbons, may also be utilized for the olefin synthesis, provided that the appropriate residence times are maintained. Such residence times are readily determined by the skilled artisan due to the inherently longer product residence time.

In order to maximize the hydrocarbon product yield in the $C_4$–$C_{20}$ carbon range, particularly the linear alpha olefin yield in the $C_4$–$C_{20}$ carbon range; the hydrocarbon synthesis reaction is preferably conducted at an alpha of less than 0.9 and more preferably less than 0.8. This is in contrast to an alpha of at least, and preferably greater than 0.9, which is desirable for synthesizing higher molecular weight hydrocarbons for fuel and lubricant applications.

In a broad embodiment, the invention relates to a process for synthesizing $C_4$–$C_{20}$ linear alpha olefins, wherein the process comprises passing a synthesis gas feed comprising a mixture of $H_2$ and CO through a linear alpha olefin hydrocarbon synthesis reactor, in which it contacts a non-shifting Fischer-Tropsch hydrocarbon synthesis catalyst comprising a catalytic cobalt component, at reaction conditions sufficient for the $H_2$ and CO to react and form the linear alpha olefins and wherein the reaction conditions are such that the following expression has a value greater than or equal to 50:

$$200-0.6(T)+0.03P_{H2O}-0.6X_{CO}-8(H_2:CO),$$

and wherein,

T=average reactor temperature in ° C.

$P_{H2O}$=partial pressure of the water in the synthesis gas feed to the reactor, in kPa $X_{CO}$=CO conversion, expressed as percent, and $H_2$:CO=hydrogen to CO molar ratio in the synthesis gas feed to the reactor.

The above expression defines the Condition Factor (CF). Thus, the preferred reaction conditions of the process of the invention can also be described as a combination of average reaction temperature, water partial pressure in the feed, CO conversion, and feed $H_2$:CO ratio that yields a CF value of greater than or equal to 50.

DETAILED DESCRIPTION

Figure 1:
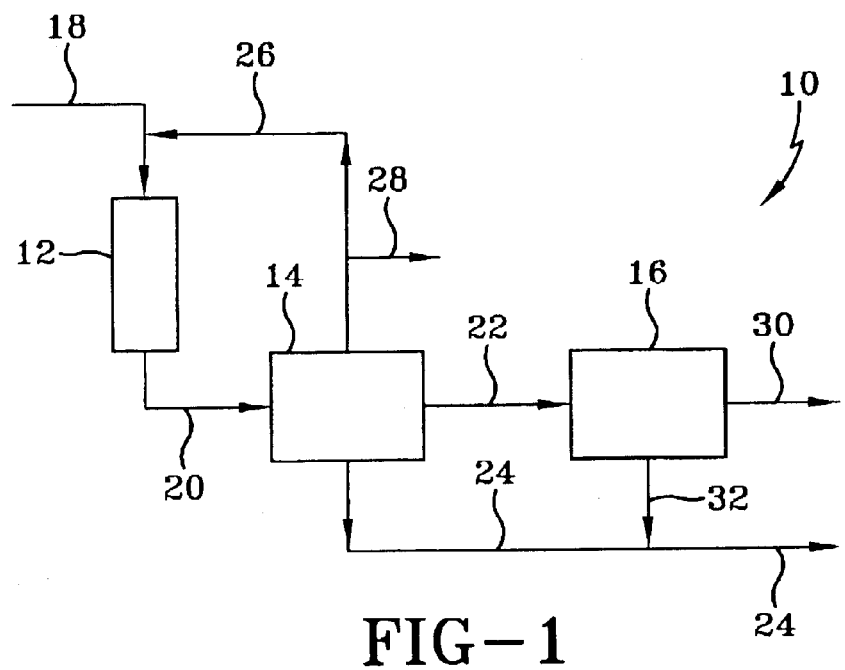
FIG. 1 is a block flow diagram of a stand-alone linear alpha olefin process of the invention.

In the process of the invention, the linear alpha olefins are produced by a Fischer-Tropsch hydrocarbon synthesis reaction in which $H_2$ and CO in the feed gas react in the presence of a non-shifting Fischer-Tropsch hydrocarbon synthesis catalyst, comprising a catalytic cobalt component, under reaction conditions defined by a Condition Factor described above as having a value greater than or equal to 50. Optionally, the process conditions are also adjusted and/or the catalyst selected to achieve a reaction alpha of less than 0.9 and preferably less than 0.8 to maximize linear alpha olefin production in the $C_4$–$C_{20}$ carbon range. By reaction alpha is meant the Schultz-Flory alpha, as is determined by the molecular weight distribution of the synthesized hydrocarbons, and may be determined as reported in J. Eilers, et. al., *The Shell Middle Distillate Synthesis Process* (*SMDS*) in *Catalysis Letters* Vol. 7 (1990) p. 253–270. At a given $H_2$ to CO mole ratio, the alpha will be reduced by (a) increasing the reaction temperature and (b) decreasing the reaction pressure.

The non-shifting hydrocarbon synthesis catalyst comprising a catalytic cobalt component used in the linear alpha olefin production process of the invention comprises unsupported cobalt, or a supported Fischer-Tropsch hydrocarbon synthesis catalyst which is a composite of cobalt or promoted cobalt and one or more support components. The preparation of an unsupported or bulk, rhenium-promoted cobalt catalyst that has been found useful for producing linear alpha olefins according to the invention is described below, in the preamble to the examples. Also described below, and which is useful for producing linear alpha olefins according to the invention, is a supported, rhenium-promoted cobalt catalyst, that has been used to produce linear alpha olefins according to the process of the invention and has also been used in slurry Fischer-Tropsch hydrocarbon synthesis reactors producing mostly (e.g., at least 90 wt. %) saturated, normal paraffin hydrocarbons having less than 6 wt. % olefins (less than 10 wt. % olefins in the synthesized $C_4$–$C_{20}$ fraction), wherein the support comprised a composite of titania and silica-alumina. Preferred supports for supported Fischer-Tropsch hydrocarbon synthesis catalysts containing a catalytic cobalt component, comprise titania, silica, and modified titania and silica, such as, for example, $ZrO_2$-modified $TiO_2$, with or without binders, for both the linear alpha olefin synthesis and for synthesizing higher molecular weight, primarily paraffinic liquid hydrocarbon products, including lubricant oil fractions. A support component comprising titania is preferred. The amount of cobalt present in supported catalysts may range from 1–50 wt. % of the catalyst, preferably 2–40 wt. % and more preferably 2–25 wt. %. If a promoter such as rhenium is used, the weight ratio of the cobalt to the promoter will range from 30:1 to 2:1 and preferably from 20:1 to 5:1. Useful catalysts and their preparation are known and illustrative, but non-limiting examples may be found, for example, in U.S. Pat. No. 5,945,459, U.S. Pat. No. 5,968,991, U.S. Pat. No. 6,090,742, U.S. Pat. No. 6,136,868, U.S. Pat. No. 6,319,960, RE 37,406, U.S. Pat. No. 6,355,593, U.S. Pat. No. 6,331,575.

The total synthesized $C_4$–$C_{20}$ hydrocarbon fraction is separated by fractionation, from the lower and higher carbon number, $C_{3-}$ and $C_{21+}$ hydrocarbons, which are also synthesized by the linear alpha olefin producing process of the invention. The separated $C_4$–$C_{20}$ hydrocarbon fraction containing the desired linear alpha olefins also contains internal olefins, paraffins, and a small amount of oxygenates formed by the synthesis reaction. It is therefore typical to further treat the linear alpha olefins to recover the desired $C_4$–$C_{20}$ linear alpha olefins, by any suitable means. All known linear alpha olefin recovery processes are quite complex and thus costly. It is therefore advantageous to make a crude alpha olefin product that has as high a concentration of the linear alpha olefins as possible, to thereby reduce the complexity and cost of recovering them. One known method for recovering linear alpha olefins from the oxygenates-containing, total synthesized $C_4$–$C_{20}$ hydrocarbon fraction, is to react the linear alpha olefins in the separated $C_4$–$C_{20}$ fraction with alkanols, to form ethers. The so-formed ethers are then separated from the rest of the hydrocarbons in the separated $C_4$–$C_{20}$ cut by fractionation. (c.f. German patent publications DE 19825295 and DE 19833941). The separated ethers are chemically treated to convert them back into linear alpha olefins. Since ethers are themselves oxygenates, the presence of oxygenates in the separated total $C_4$–$C_{20}$ hydrocarbon fraction increases the difficulty and cost of recovering the linear alpha olefins by this process. Therefore, a significant advantage of the process of the present invention is the very low levels of oxygenates of less than 3 wt. % and preferably less than 1 wt. % that it produces in the total $C_4$–$C_{20}$ hydrocarbon fraction synthesized by the process. This low oxygenates level is much lower than the typical amount of at least 8–10 wt. % oxygenates made using iron-based Fischer-Tropsch hydrocarbon synthesis catalysts. The total oxygenate content may be determined by gas chromatography or by high-resolution NMR. Another known method for separating linear alpha olefins from saturated hydrocarbons and internal olefins in the same boiling point range may be found, for example, in U.S. Pat. No. 5,877,378. In this process, which is also adversely affected by the presence of oxygenates (e.g., alcohols and acids), the linear alpha olefins are selectively converted to trialkylaluminum compounds, which are then separated from the unconverted other hydrocarbons and converted back into ethers. The low oxygenates content and high level of linear alpha olefin production obtained in the practice of the invention, results in significantly lower cost to recover the linear alpha olefin products by this method as well.

The linear alpha olefin producing process of the invention can be integrated into a Fischer-Tropsch hydrocarbon synthesis process plant (integrated process) or it may comprise a separate facility with its own source of synthesis gas (stand-alone process). As mentioned under the summary, it is preferred that all process embodiments comprise gas conversion processes, which include production of the synthesis gas feed from natural gas. Syngas derived from natural gas provides the desired stoichiometry for the linear alpha olefin synthesis process of the invention which utilizes a non-shifting cobalt-based Fischer-Tropsch synthesis catalyst. The linear alpha olefin production process of the invention is also a type of Fischer-Tropsch hydrocarbon synthesis process, but one that maximizes olefin production to at least 50 wt. % of the total synthesized hydrocarbons, i.e., at least 50 wt. % of the total synthesized $C_4$–$C_{20}$ hydrocarbons produced in the linear alpha olefin reactor are linear alpha olefins. This distinguishes it from what is referred to herein as a hydrocarbon synthesis process, which produces mostly (e.g., at least 85 wt. %) saturated, i.e., paraffinic hydrocarbons overall, with typically less than 5 wt. % linear alpha olefins in the synthesized $C_4$–$C_{20}$ hydrocarbon fraction. Therefore, for the sake of convenience and in the context of the invention, the latter process is referred to herein as a hydrocarbon synthesis process, while the process described herein as having a CF greater than or equal to 50 is referred to as a linear alpha olefin synthesis process.

In an integrated linear alpha olefin and hydrocarbon synthesis (HCS) process of the invention, synthesis gas is fed to either the LAO or HCS reactor. The tail gas from the reactor can then be utilized as feed gas for the other reactor. Additionally, products from one of the two processes (hydrocarbon synthesis and linear alpha olefin synthesis) may be combined with products from the other process.

Preferably in an integrated process syngas having e.g. an $H_2$:CO mole ratio of 2:1 is passed to an HCS reactor and syngas having an $H_2$:CO mole ratio of lower than 2:1 is passed to an LAO reactor because the consumption ratio of the LAO process is 2:1 the tail gas from the LAO reactor will be CO rich and $H_2$ poor or depleted. The tail gas from both units can then be combined to provide a feed gas to the LAO reactor having a more preferred $H_2$:CO mole ratio of lower than 2:1. In this manner, an integrated process is achieved. Alternatively, the tail gas from the HCS reactor can be used alone as feed gas to the LAO reactor.

One or more reactors for producing linear alpha olefins according to the practice of the invention may be erected as part of a hydrocarbon synthesis plant, added to it later or be one or more hydrocarbon synthesis reactors that have been temporarily or permanently switched to linear alpha olefin production. In another integrated linear alpha olefin process embodiment, in a plant or facility (these two terms are used synonymously) built for linear alpha olefin production, one or more hydrocarbon synthesis reactors may be added to it or one or more linear alpha olefin producing reactors may be temporarily or permanently switched to hydrocarbon synthesis reactor. In an embodiment in which a hydrocarbon synthesis reactor contains a non-shifting synthesis catalyst comprising a catalytic cobalt component, replacement of the catalyst will not be necessary when switching it over from hydrocarbon synthesis to linear alpha olefin synthesis providing a unique benefit. Further, when switching a linear alpha olefin synthesis reactor to hydrocarbon synthesis, it will not be necessary to change the catalyst in the reactor for the switchover.

In one specific embodiment of an integrated linear alpha olefin synthesis process of the invention, one or more linear alpha olefin synthesis reactors will use tail gas from one or more Fischer-Tropsch hydrocarbon synthesis reactors, as all or part of the synthesis gas used for producing the linear alpha olefins and vice-versa. By way of an illustrative, but nonlimiting example of this type of embodiment, at least two synthesis reactors are used, with at least one reactor, a Fischer-Tropsch hydrocarbon synthesis reactor upstream of the linear alpha olefin reactor, operating with a non-shifting cobalt hydrocarbon synthesis catalyst comprising a catalytic cobalt component and a support component, at a reaction alpha high enough (e.g., $\geq 0.9$) to produce both fuel and lubricant oil hydrocarbon fractions, from a synthesis gas feed (preferably produced from natural gas) in which the $H_2$:CO mole ratio is less than the stoichiometric (2.1:1) $H_2$:CO consumption ratio (e.g., 2.0:1 or less) and the reactor is operating at a high CO conversion level (e.g., 80% or higher). The hydrocarbon synthesis reactor may be a slurry reactor, a fixed bed reactor or a fluid bed reactor. A slurry reactor is preferred for maximizing higher molecular weight hydrocarbons boiling in the lubricant oil range. Both the linear alpha olefin and hydrocarbon synthesis reactors of the integrated linear alpha olefin process may contain the same or different non-shifting hydrocarbon synthesis catalyst comprising a catalytic cobalt component. The hydrocarbon synthesis reactor produces a reactor tail gas containing unreacted $H_2$ and CO, having a reduced $H_2$:CO mole ratio. After removing at least a portion of the $C_{2+}$ hydrocarbons and (optionally) $H_2O$ from the tail gas, the remainder containing the reduced (e.g., 1:1) mole ratio $H_2$:CO, is passed into the linear alpha olefin synthesis reactor. The conditions of the linear alpha olefin synthesis reactor is set so that the CF value, which incorporates the aforementioned reduced feed ratio, is higher than 50. In yet another illustration of an integrated process embodiment of the invention, a synthesis gas producing unit is producing, from natural gas, a synthesis gas containing $H_2$ and CO in a mole ratio of at least 2:1, as feed for one or more hydrocarbon synthesis reactors. A portion or slip stream of this synthesis gas is passed to either physical or chemical separation means, for removing some of the hydrogen from the synthesis gas, to produce a hydrogen-reduced synthesis gas in which the $H_2$:CO mole ratio is less than 2.1:1 (e.g. 1:1). This hydrogen-reduced synthesis gas is passed into one or more linear alpha olefin synthesis reactors. The conditions of the linear alpha olefin synthesis reactor is again set so that the CF value is greater than or equal to 50. Physical separation processes (means) for separating $H_2$ from the synthesis gas include adsorption-desorption, membrane separation and a combination thereof, all of which are well known and commercially available. Adsorption-desorption processes include temperature swing adsorption (TSA) and pressure swing adsorption (PSA), both of which comprise a plurality of adsorbent containing vessels operated in a cyclic manner. Chemical means includes a water gas shift reactor, which is typically combined with physical separation means.

Synthesis gas for the process of the invention is preferably produced from natural gas, which can comprise as much as 92 mole % methane, with the remainder primarily $C_{2+}$ hydrocarbons, nitrogen and $CO_2$. Methane has a 4:1 H:C ratio and is therefore ideal for producing, preferably by a combination of partial oxidation and steam reforming, a synthesis gas having an $H_2$:CO mole ratio of nominally 2.1:1, which is the stoichiometric mole ratio used with a non-shifting cobalt catalyst for hydrocarbon synthesis. Sulfur and other heteroatom compounds are removed from the natural gas, and in some cases also nitrogen and $CO_2$. The remaining methane-rich gas, along with oxygen or air and steam, is passed into a synthesis gas generator. Oxygen is preferred to air, because it does not introduce nitrogen into the synthesis gas generator (reactor). During the synthesis gas reaction, nitrogen can form HCN and $NH_3$, both of which are poisons to a cobalt Fischer-Tropsch catalyst and must therefore be removed down to levels below 1 ppm. If nitrogen is not removed from the natural gas, and/or if air is used as the source of oxygen, HCN and $NH_3$ must be removed from the synthesis gas, before it is passed into a hydrocarbon synthesis reactor. Known processes for synthesis gas production include autothermal reforming and fluid bed synthesis gas generation, both of which employ oxygen and form the synthesis gas by partial oxidation and catalytic steam reforming. A review of these and other processes for producing synthesis gas and their relative merits, may be found, for example, in U.S. Pat. No. 5,883,138.

Due to the nature of the surface chemistry involved, hydrogen to carbon monoxide mole ratios of typically less than 2:1 are preferred preferably less than 1.8:1, more preferably about 1:1 in the feed to the reactor for achieving a preferred CF value of greater than or equal to 50 and thus producing linear alpha olefins with high selectivity over a non-shifting synthesis catalyst comprising a catalytic cobalt component. However, the stoichiometric $H_2$:CO mole ratio of the $H_2$ and CO consumed by the linear alpha olefin synthesis reaction is 2:1 and the consumption of the CO in the synthesis gas feed gas by the reaction in a single pass through the synthesis reactor is typically less than 50%. This means the linear alpha olefin synthesis gas reactor produces a tail gas which (i) is rich in valuable, unreacted CO, (ii) depleted in $H_2$ and (iii) has an $H_2$:CO mole ratio below that in the feed gas passed into the reactor. At least a portion of this tail gas, comprising the unreacted CO and hydrogen, is recycled back to the linear alpha olefin synthesis reactor, along with the incoming, fresh synthesis gas feed. The fresh makeup gas fed to the process will typically have a higher $H_2$:CO ratio than the $H_2$:CO ratio in the feed to the reactor if such recycle of the linear alpha olefin synthesis reactor effluent gas is applied, and will essentially follow the stoichiometry of the linear alpha olefin synthesis process, i.e., typically 2:1. It is important to understand that in cases when there is an effluent recycle, the $H_2$:CO ratio used in calculating the Condition Factor is not that of the make-up gas but instead the $H_2$:CO ratio of the feed to the linear alpha olefin synthesis reactor. The feed to the reactor is generated by blending the recycle and make-up gas streams, thus the reactor feed typically has lower than 2:1 $H_2$:CO ratio due to the $H_2$-deficiency of the recycled tailgas component Hydrogen may be separated from synthesis gas having a relatively high $H_2$:CO mole ratio of, e.g., 2:1, or 2.1:1, to produce hydrogen and a synthesis gas having a lower $H_2$:CO mole ratio. One or more of the higher or lower mole ratio synthesis gases, and separated hydrogen, may be combined with the recycled CO-rich tail gas, to provide the desired $H_2$:CO mole ratio in the combined synthesis gas stream fed into the linear alpha olefin synthesis reactor. It is understood, however, that regardless of the feed $H_2$:CO ratio to the reactor, the $H_2$:CO consumption ratio of the linear alpha olefin process of the invention is 2:1. This consumption ratio is close to the 2.1:1 ratio needed for the conventional hydrocarbon synthesis process carried out with non-shifting cobalt-based catalysts making paraffinic fuel and lubrication products. As discussed earlier, the $H_2$:CO ratio in synthesis gas derived from natural gas is also 2:1, and thus in line with the consumption ratio of both the conventional hydrocarbon synthesis and the linear alpha olefin synthesis processes. Consequently, the use of natural gas to produce synthesis gas is preferred for both linear alpha olefin process of the invention and those embodiments in which it is integrated with hydrocarbon synthesis.

Fischer-Tropsch hydrocarbon synthesis processes are well known and comprise contacting a synthesis gas comprising a mixture of $H_2$ and CO with a Fischer-Tropsch synthesis catalyst, at reaction conditions effective for the $H_2$ and CO react to form hydrocarbons under shifting or non-shifting conditions. For the linear alpha olefin synthesis process of the invention, non-shifting conditions and a non-shifting catalyst are used. This means that less than 5 and preferably less than 1 wt. % of the CO in the synthesis gas feed is converted to $CO_2$ in one pass of the synthesis gas through the reactor. Fischer-Tropsch types of catalysts for hydrocarbon synthesis may comprise, for example, one or more Group VIII catalytic metals such as Fe, Ru, Co, and Ni, and optionally one or more promoters such as Re, Pt, Th, Zr, Hf, U, Mg and La, on a suitable inorganic support material, preferably one that comprises one or more refractory metal oxides. A non-shifting catalyst in which the catalytic metal component comprises cobalt is used in the linear alpha olefin reactor of the invention and this typically excludes the use of iron in the catalyst. Some of the synthesized hydrocarbons will be liquid, some solid (e.g., wax) and some gas at ambient conditions of temperature and pressure, particularly if a catalyst having a catalytic cobalt component is used. Slurry Fischer-Tropsch hydrocarbon synthesis processes are often preferred for producing relatively high molecular weight, paraffinic hydrocarbons when using a cobalt catalyst, but not for producing the linear alpha olefins. The $H_2$:CO mole ratio for a hydrocarbon synthesis process may broadly range from about 0.5 to 4, but is more typically falls within the range of from about 0.7 to 2.75. These $H_2$:CO mole ratio ranges are achieved by the type of reaction and reaction conditions used to produce the FIG. 1 is a simple block flow diagram of a stand-alone linear alpha olefin process of the invention. Plant 10 comprises a fixed bed, down-flow linear alpha olefin reactor 12, which synthesizes $C_4$–$C_{20}$ linear alpha olefins (and also other hydrocarbons such as $C_4$–$C_{20}$ paraffins and internal olefins, $C_{3-}$ and $C_{21-}$ hydrocarbons, etc.) and separation units 14 and 16. Synthesis gas comprising $H_2$ and CO is passed, via line 18, from a synthesis gas generating unit (not shown) which includes gas clean-up to remove sulfur, HCN and $NH_3$ from the gas, into reactor 12 which contains one or more fixed beds of the non-shifting Fischer-Tropsch catalyst. In this illustration, the catalyst comprises unsupported, rhenium promoted, particulate cobalt. In reactor 12, the $H_2$ and CO in the synthesis gas react in the presence of the catalyst to form linear alpha olefins, including $C_4$–$C_{20}$ linear alpha olefins (and also saturated paraffins). Reactor 12 operates at reaction conditions that meet the criteria for the Condition Factor (CF) to be greater than or equal to 50 which, in this non-limiting illustration, includes a synthesis gas $H_2$:CO mole ratio of 1:1, a CO conversion of 12–15%, a temperature of 205° C., a synthesis gas feed space velocity of 38,000 V/V/hr, a pressure of 2000 kPa. The synthesized hydrocarbons and unreacted synthesis gas pass down out of the reactor and are removed at the bottom by line 20. The mixture of hydrocarbons and gas passes into separation unit 14, in which the gas is separated from the hydrocarbons and the hydrocarbons are separated into a $C_{20-}$ fraction and a $C_{20+}$ fraction. The unreacted synthesis gas is removed from 14 via line 26 and recycled back into hydrocarbon synthesis reactor 12, via line 18, in which it mixes with the fresh synthesis gas feed coming from the synthesis gas generating unit. Some of the gas is purged via line 28, to prevent build-up of normally gaseous hydrocarbons (e.g., $C_1$–$C_4$) in the recycle gas. The $H_2$:CO mole ratio in the synthesis gas produced in the synthesis gas generator is adjusted so that the mixture of the fresh synthesis gas and recycle gas, entering reactor 12, contains $H_2$ and CO in the desired $H_2$:CO mole ratio which, in this illustration, is 1:1. Separation unit 14 contains the necessary coolers and separator drums to condense the water and hydrocarbons produced by the synthesis reaction and to and separate the water, unreacted synthesis gas and gaseous hydrocarbons, and liquid hydrocarbons. If desired or necessary, the separated water is used to humidify the feed gas in line 18, to increase the partial pressure of the water in the feed being passed into reactor 12. The liquid hydrocarbons are also separated in 14 by fractionation into the $C_{21+}$ hydrocarbons and the linear alpha olefin-containing $C_{20-}$ fraction. The $C_{20-}$ fraction is removed from 14 via line 22 and passed into linear alpha olefin separator 16. The $C_{20-}$ fraction is removed from 14 via line 24. In unit 16, the linear alpha olefins are separated from the other components of the $C_{20-}$ hydrocarbon fraction. There are several methods known in the art for recovering linear alpha olefins from Fischer-Tropsch synthesized hydrocarbon streams and any of these methods is applicable for the recovery of the product $C_4$–$C_{20}$ alpha olefins of the invention. Typically, the linear alpha olefins are selectively converted into another entity, like ethers (c.f, German patent publications DE 19825295 and DE 19833941) or metal alkyls, like alkyl aluminum (U.S. Pat. No. 5,877,378). These chemically transformed linear alpha olefin derivatives in turn are separated from the rest of the unconverted $C_{20-}$ hydrocarbons, such as paraffins and internal olefins, etc., by fractionation. Finally, the separated linear alpha olefin derivatives are chemically converted back into linear alpha olefins. The linear alpha olefin products are removed from the linear alpha olefin recovery unit 16 via line 30 and the rest of the $C_{20-}$ hydrocarbons via line 32, from which they are passed into line 24, in which they are combined with the $C_{21+}$ hydrocarbons. Line 24 passes these combined $C_{21+}$ and $C_{20-}$ hydrocarbons to further processing.

Figure 2:
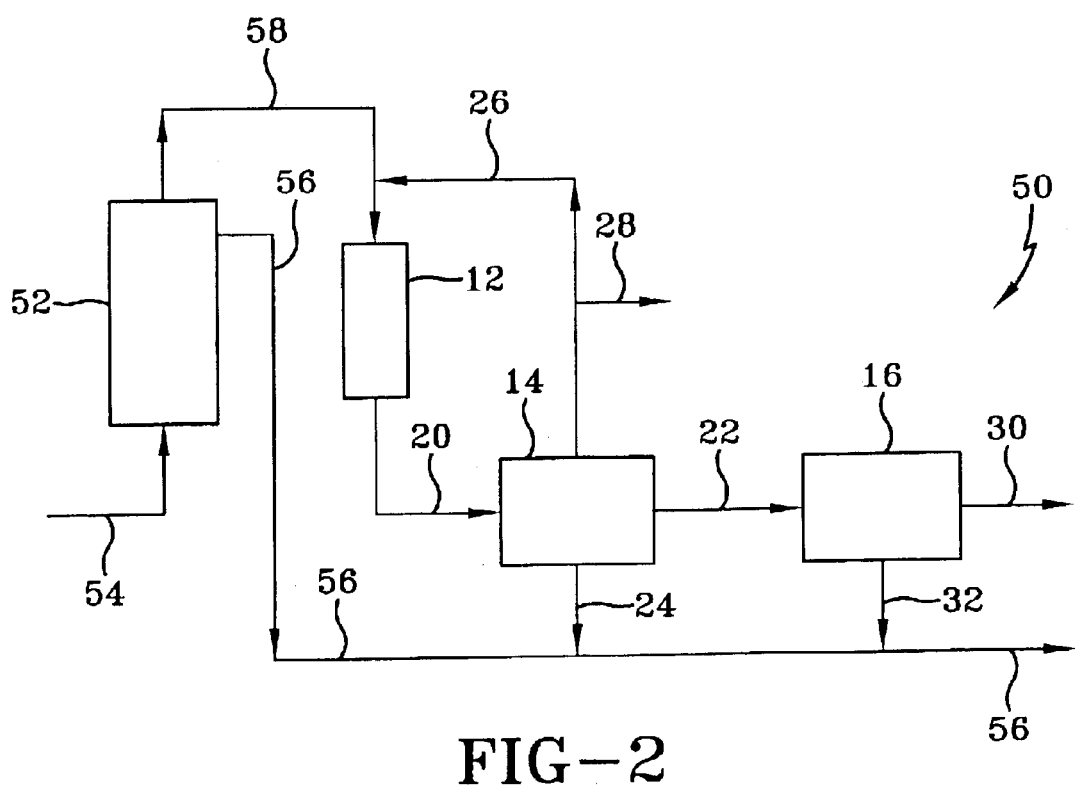
FIG. 2 is a block flow diagram of one embodiment of an integrated linear alpha olefin and hydrocarbon synthesis process of the invention.

In FIG. 2, an integrated linear alpha olefin synthesis unit 50 comprises a slurry hydrocarbon synthesis reactor 52, a linear alpha olefin synthesis reactor 12, and separation units 14 and 16. Reactor 12 and units 14 and 16 are the same as in FIG. 1, as are the flow lines having the same numbers as in FIG. 1. Slurry hydrocarbon synthesis reactor 52 contains a hydrocarbon slurry within in which is dispersed a particulate Fischer-Tropsch hydrocarbon catalyst comprising rhenium-promoted cobalt on a titania support (e.g. 11 wt. % Co and 1 wt. % Re, based on the total catalyst weight). Examples of useful catalysts for hydrocarbon synthesis are described, for example, in U.S. Pat. No. 5,9451459, U.S. Pat. No. 5,968,991, U.S. Pat. No. 6,090,742, U.S. Pat. No. 6,136,868, U.S. Pat. No. 6,319,960, RE 37,401, U.S. Pat. No. 6,355,593, U.S. Pat. No. 6,331,575. In this embodiment, a synthesis gas feed comprising $H_2$ and CO in a 2.1:1 mole ratio is passed up into reactor 52 via line 54. Reactor 52 operates at an alpha of $\geq 0.9$ and produces mostly (e.g., $\geq 90$ wt. % paraffins), including hydrocarbons boiling in the fuels and lubricant ranges. The CO conversion in the reactor is 80% in a single pass. The synthesized hydrocarbons that are liquid at the reaction conditions are separated from the catalyst particles in 52 via filtration (not shown) and removed from the reactor via line 56. The unreacted synthesis gas, which now contains $H_2$ and CO in a lower than 2:1 mole ratio (preferred for linear alpha olefin synthesis), is removed from the reactor via line 58 and passed into linear alpha olefin synthesis reactor 12. Some of the hydrocarbon synthesis reaction water may be removed from the unreacted synthesis gas, to adjust the water vapor pressure in the linear alpha olefin synthesis gas feed stream 58, to the desired level. Most of the $C_{4+}$ hydrocarbons are also removed before the gas is passed into reactor 12. Reactor 12 and units 14 and 16 are the same as for FIG. 1, and their operation and function need not be repeated here. Thus, the linear alpha olefins produced in reactor 12 are removed from 16 via line 30. However, the other $C_{20+}$ and $C_{20-}$ hydrocarbons synthesized in 12, and removed from 14 and 16 via lines 24 and 32 (as in FIG. 1), are passed into line 56, in which they mix with the liquid hydrocarbons removed from the hydrocarbon synthesis reactor 52. This mixture is passed to upgrading operations.

Figure 3:
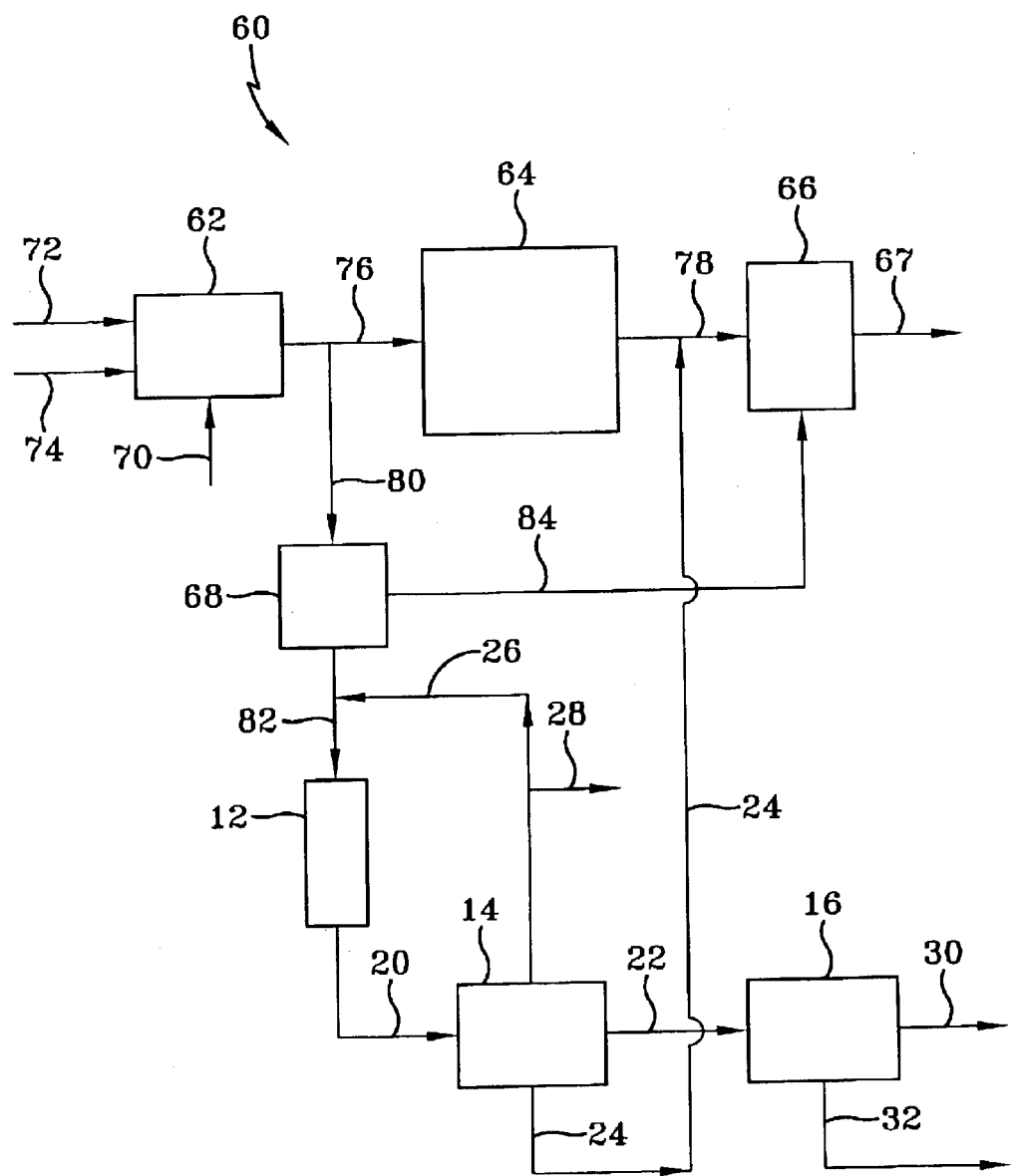
FIG. 3 is a block flow diagram of one embodiment of another integrated linear alpha olefin and hydrocarbon synthesis process of the invention.

Turning now to FIG. 3, an integrated gas conversion plant 60 comprises a synthesis gas generating unit 62, a hydrocarbon synthesis unit 64, a hydrocarbon upgrading unit 66 and a hydrogen separating unit 68, along with a linear alpha olefin hydrocarbon synthesis reactor 12 and associated linear alpha olefin product separation units 14 and 16. Units 12, 14, 16 and associated flow lines are the same as in FIGS. 1 and 2. Natural gas, oxygen and steam are fed into the synthesis gas generating unit 62 via lines 70, 72 and 74, respectively, to generate a synthesis gas, from natural gas, comprising a mixture of $H_2$ and CO having a 2.1:1 mole ratio, by a combination of partial oxidation and steam reforming. Part of this gas is fed into unit 64 via line 76. The hydrocarbon synthesis unit 64 contains one or more hydrocarbon synthesis reactors producing hydrocarbons boiling primarily in the lubricant oil and fuels boiling ranges. Each reactor contains a hydrocarbon synthesis catalyst such as, for example, a rhenium-promoted cobalt catalytic component supported on titania. The unit also contains heat exchangers and separation drums for cooling and separating out the synthesis reaction water from the $C_{4+}$ hydrocarbons in the gas. The synthesized $C_{4+}$ hydrocarbons are passed, via line 78, from unit 64 to hydrocarbon upgrading unit 66. Unit 66 contains one or more fractionators, as well as one or more hydrotreating reactors, such as isomerization units to lower the pour point of the paraffinic hydrocarbons. The upgraded hydrocarbons are removed from 66 via line 67. A synthesis gas slip-stream is withdrawn from line 76, via line 80, and passed into unit 68. Unit 68 separates hydrogen from the synthesis gas to produce a stream of CO-enriched synthesis gas, which is removed from 68, via line 82. The $H_2$:CO mole ratio in this gas stream is such that, when mixed with recycled, unreacted synthesis gas from reactor 12, the $H_2$:CO mole ratio of the feed gas entering 12 is lower than 2:1, preferably lower than 1.8:1 and more preferably about 1:1. This combined feed stream is passed into the alpha olefin synthesis reactor 12 via line 82. Reactor 12 operates at reaction conditions, as in the embodiment of FIG. 1 and includes the low $H_2$:CO mole ratio in the feed gas, to satisfy the requirement of the Condition Factor being greater than or equal to 50. Reactor 12 produces linear alpha olefins at a high yield which, along with the unreacted synthesis gas, is passed to separation unit 14, via line 20. If the desired alpha olefin fraction falls in the carbon number range of 4 to 20, it is preferred to make hydrocarbons in reactor 12 that boil primarily in the naphtha and lower fuels boiling ranges. The hydrogen separated in unit 68 is passed to the hydrocarbon upgrading unit 66, via line 84. Unreacted synthesis gas separated in 14 is passed via line 26, back into line 82 in which it mixes with the CO-enriched gas formed in 68. As in FIGS. 1 and 2, a portion of the recycled gas is purged via line 28 and is used as low BTU fuel gas or reused for synthesis gas generation in 62. The $C_{21+}$ hydrocarbons produced in 12, and separated from the $C_{20-}$ linear alpha olefins in 14, are removed from 14 via line 24 and passed to line 78, for further processing in unit 66. The linear alpha olefin product of reactor 12 is removed from unit 16 via line 30. Line 32 passes the $C_{20-}$ hydrocarbons separated from the $C_{20-}$ linear alpha olefins to further processing for naphtha and low BTU value fuels.

At least a portion of the hydrocarbons produced by a hydrocarbon synthesis process, including the saturates produced by the linear alpha olefin production process according to the invention, are upgraded to more valuable products. The upgrading comprises one or more of fractionation and conversion. By conversion is meant one or more operations in which the molecular structure of at least a portion of the hydrocarbon is changed and typically in the presence of al catalyst. Hydrotreating is a conversion in which hydrocarbons are reacted wit hydrogen in the presence of a catalyst and includes, for example, hydroisomerization, hydrocracking, hydrodewaxing, hydrorefining, all conducted at conditions well known in the literature. In the context of the invention, conversion also refers to chemically treating the linear alpha olefins to separate them from the other hydrocarbons in the separated $C_4$–$C_{20}$ fraction and treating the separated material to convert it back to the desired linear alpha olefin product, by any suitable means, including the etherification and metal alkylation procedures mentioned above.

The invention will be further understood with reference to the examples below.

EXAMPLES

In all of the examples, the reactors were downflow, isothermal tube reactors containing a fixed bed of particulate catalyst (particle size below 80 mesh), held in place by quartz wool. The catalyst bed was diluted with below 80 mesh quartz or SiC to ensure isothermal conditions. In all cases they were operated at a total pressure of 20 atmospheres (2000 kPa), with a synthesis gas flow rate of either 6,000 or 40,000 V/V/hr. The synthesis gas fed into the reactor comprised of $H_2$ and CO as the reactants, along with Ar and/or Ne as a diluent and internal standard for establishing mass balances. An He diluent was also used to balance the total pressure of the reactants and internal standards. The mass balances were calculated from the feed flow rates combined with feed and product compositions obtained by gas chromatography (GC) or GC-mass-spectrometric (GC-MS) analysis. CO conversions were calculated by known methods of using internal standards. The Hewlett-Packard 5890 GC and Balzers TGG 300 MS coupled to the Hewlett-Packard 5890 GC (GC-MS mode) were calibrated using certified gas blends. The $H_2$ to CO mole ratio varied from 1:1 to more than 2:1. The CO conversion was adjusted in all experiments to the target 12% level by adjusting the feed rate. In two of the runs, those of Examples 7 and 8, the catalyst comprised rhenium-promoted cobalt on titania (11 wt % Co, 1 wt. % Re), of the type used for Fischer-Tropsch hydrocarbon synthesis in a slurry synthesis reactor. The rest of the examples, Examples 1–6, used an unsupported, rhenium-promoted cobalt catalyst. This catalyst was prepared by impregnating cobalt powder with an activating solution of cobalt nitrate and perrhenic acid. The impregnation solution was prepared by dissolving 26.3 g of $Co(NO_3)_2$ and 2.3 g perrhenic acid (54 wt. % Re) in 9.4 g of distilled and deionized water. An amount of 34.8 g of this solution was slowly added, with constant mixing, to 50.2 g of 2 micron size cobalt powder. The exothermic reaction was controlled by the slow addition rate and stirring. The addition took place over thirty minutes. The treated cobalt powder was then dried in air at 60° C. for four hours. The dry powder was then calcined using 1 vol. % oxygen in dry nitrogen, by slowly ramping, at 2° C./min to 300° C. and then held at 300° C. for one hour. After cooling, the dry powder was loaded into the reactor for the hydrocarbon synthesis runs. The conditions and results of the eight runs are summarized in the table below.

Example 1

In this experiment, the reactor was operated at 210° C., the mole ratio of the $H_2$ to CO in the synthesis gas feed was 1:1 and the unsupported cobalt catalyst described above was used for the synthesis. The partial pressure of both the $H_2$ and CO in the reactor was 500 kPa. The CF value in this experiment was 59.

Example 2

In this experiment, the effect of temperature was tested by operating the reactor at 221° C. All other conditions were the same as in Example 1. The CF value in the experiment was 52.

Example 3

In this experiment, the effect of the $H_2$:CO ratio was tested. The reactor was operated at the same conditions as in Example 1, except for the feed $H_2$ and CO partial pressures, which were 500 kPa and 250 kPa, respectively. The CF value for the run was 51.

Example 4

In this experiment, the effect of the total synthesis gas pressure was tested. The reactor was operated at the same conditions as in Example 1, except for the partial pressures of $H_2$ and CO in the reactor feed, which were both only 250 kPa instead of the 500 kPa in Example 1. The CF value was 59.

Example 5

The effect of $H_2O$ vapor in the feed gas was demonstrated in this experiment. The reactor was operated as in Example 3, except that in this run 400 kPa steam was added to the feed gas by replacing an equal concentration (partial pressure) of the inert diluent in the feed. The CF value in the experiment was 63.

Comparative Examples 6, 7, and 8 (Outside the Scope of the Invention)

Example 6

This experiment demonstrates that reduced CO conversion alone will not ensure high olefin selectivity, if the CF value is not above 50. The respective partial pressures of the $H_2$ and CO in the reactor were 1000 kPa and 500 kPa, providing a $H_2$:CO ratio of 2:1 in the dry feed gas. The CO conversion was set to 12%, just as in Examples 1–5. The temperature was 220° C. The overall CF value in this experiment was 45.

Example 7

In this experiment, the catalyst was different from those used in Examples 1–6 and comprised the rhenium-promoted cobalt (11 wt. % Co, 1 wt. % Re) catalytic component supported on titania. The reactor was operated at the same conditions as in Example 6: 220° C., the mole ratio of the $H_2$ to CO in the synthesis gas feed was 2:1 and the respective partial pressures of the $H_2$ and CO in the reactor were 1000 kPa and 500 kPa, respectively. Consequently, the CF value in the experiment was also the same as in Example 6, i.e., 45.

Example 8

The same rhenium-promoted cobalt on titania catalyst used in Example 7 was also used in this experiment. The reactor was operated at a similar temperature of 219° C., the mole ratio of the $H_2$ to CO in the synthesis gas feed was about 2.2:1 and the respective partial pressures of the $H_2$ and CO in the reactor were 1420 kPa and 650 kPa. No $H_2O$ vapor was used in the feed gas. However, while the CO conversion for Examples 1–7 was low, only 12%, in this experiment it was closer to typical hydrocarbon synthesis conditions, namely 61%. The CF value in this experiment was the lowest, 15.

| Exp # | Catalyst | Temp. ° C. | CO conv. % | $P_{H2}$ kPa | $P_{CO}$ kPa | CF* | $P_{H2O}$ kPa | 1-alkene in $C_4$–$C_{10}$ % | 1-octene/ octane |
|---|---|---|---|---|---|---|---|---|---|
| 1 | Co | 210 | 12 | 500 | 500 | 59 | 0 | 61 | 1.92 |
| 2 | Co | 221 | 12 | 500 | 500 | 52 | 0 | 62 | 1.76 |
| 3 | Co | 210 | 12 | 500 | 250 | 51 | 0 | 55 | 1.18 |
| 4 | Co | 210 | 12 | 250 | 250 | 59 | 0 | 64 | 1.94 |
| 5 | Co | 210 | 12 | 500 | 250 | 63 | 400 | 66 | 1.99 |
| 6 | Co | 220 | 12 | 1000 | 500 | 45 | 0 | 26 | 0.32 |
| 7 | Co—Re/$TiO_2$ | 220 | 12 | 1000 | 500 | 45 | 0 | 35 | 0.34 |
| 8 | Co—Re/$TiO_2$ | 219 | 61 | 1420 | 650 | 15 | 0 | 18 | 0.13 |

Note:
$CF = 200 - 0.6T + 0.03P_{H2O} - 0.6X_{CO} - 8(H_2:CO)$
where,
T = average reactor temperature in ° C.
$P_{H2O}$ = partial pressure of the water in the synthesis gas feed to the reactor in kPa
$X_{CO}$ = CO conversion, expressed as percent
$H_2$:CO = Hydrogen to CO molar ratio in the synthesis gas feed to the reactor In Experiments 1–5, all of which fall within the scope of the invention, oxygen ate selectivity was negligible, in that no oxygenates were detected in the synthesized $C_4$–$C_{10}$ hydrocarbon products by gas chromatography using a flame-ionization detector. $CO_2$ selectivities were also negligible in all runs, typically around 0.5% or less, clearly affirming the non-shifting nature of the cobalt catalysts used.

Referring now to the data in the Table, it is seen that Examples 1 and 2 were both run at an $H_2$:CO mole ratio of 1:1, with the partial pressure of both the $H_2$ and CO being 500 kPa, but at different temperatures. Comparing the results for these two runs reveals that both temperatures produced about the same amount of linear alpha olefins in the $C_4$–$C_{10}$ hydrocarbon fraction synthesized in the reactor, suggesting a relatively small effect of temperature on the alpha olefin selectivity. The lower synthesis temperature of 210° C.

produced a slightly greater selectivity for $C_8$ linear alpha olefins. Overall, however, this comparison shows that the reaction temperature can be used for adjusting the Fischer-Tropsch synthesis alpha and thus increasing the total alpha olefin yield, particularly in the lower boiling range.

The Example 3 results reveal that increasing the $H_2$:CO mole ratio from 1:1 up to 2:1 resulted in a significant decrease in the linear alpha olefin content of the synthesized $C_4$–$C_{10}$ hydrocarbon fraction, from about 62% down to 55%, with an even greater decrease in $C_8$ olefin selectivity from 1.92 down to 1.18. The reduced alpha olefin yield and selectivity correlates well with the borderline CF value of 51. This example also clarifies that low CO conversion alone is an insufficient condition for high alpha olefin selectivity and yield. On the other hand, the value Condition Factor a of the invention can define the operating conditions and predict the high alpha olefin yield.

A comparison of the Example 4 results with those of Example 1, which differ only by the pressure of the $H_2$ and CO reactants, shows that changing the partial pressures of both the $H_2$ and CO reactants in the feed does not adversely effect either the total fraction of linear alpha olefins in the $C_4$–$C_{10}$ hydrocarbon fraction or the selectivity for $C_8$ linear alpha olefins. Comparing the results from Examples 5 and 3 clearly demonstrates the beneficial effect of adding $H_2O$ vapor to the feed gas. The 400 kPa water in the feed gas compensated for the higher $H_2$:CO mole ratio of 2:1. Thus, the linear alpha olefin content of the $C_4$–$C_{10}$ hydrocarbon fraction jumped from the 55% results of Example 3, up to 66% in the run of Example 4. At the same time, the selectivity for the $C_8$ linear alpha olefin increased from 1.18 up to 1.99, an almost two-fold increase. Again, this example demonstrates that the selection of the preferred conditions for making linear alpha olefins is not obvious and that select operating conditions which result in a Condition Factor of the invention having a value greater than or equal to 50, can provide high yields of the desired linear alpha olefins.

Comparative Examples 6–8 were all run at the higher reaction temperature of about 220° C. and the less desirable, higher $H_2$:CO reactant mole ratio of at least 2:1, at both low (12%) and high (61%) CO conversion. These runs demonstrate that the alpha olefin selectivity abruptly drops when the Condition Factor falls below the critical value of 50. They also compare the unsupported rhenium-promoted Co catalyst with the rhenium-promoted cobalt (11 wt. % Co and 1 wt. % Re) on titania catalyst used for Fischer-Tropsch hydrocarbon production. At the same CO conversion level of 12%, the supported Fischer-Tropsch hydrocarbon synthesis catalyst of Example 7 produced more linear alpha olefins than did the unsupported Re-Co catalyst of Example 6. This has two has consequences. The first is that a conventional, supported Fischer-Tropsch catalyst can be used for linear alpha olefin production. The second is that the reaction and feed conditions in a Fischer-Tropsch reactor, that is on-line synthesizing distillate fuel and lubricant oil hydrocarbons with a supported cobalt catalyst, can be adjusted to increase linear alpha olefin production without taking the reactor off line to change the catalyst, and vice-versa. Thus, if a Fischer-Tropsch hydrocarbon synthesis process plant is in existence or planned, another synthesis unit for producing linear alpha olefins can be included, without the need for a separate unit or plant for producing the hydrogen and carbon monoxide gas mixture. Linear alpha olefin synthesis can be accomplished by setting the operating conditions so that the earlier value of the Condition Factor is greater than or equal to 50.

The worst alpha olefin selectivity was obtained in Example 8, in which the total partial pressure of the $H_2$ and CO reactants was 2070 kPa, the $H_2$:CO mole ratio was about 2.2:1 and the CO reactant conversion rate was a much higher 61%. Example 8 represents conventional hydrocarbon synthesis conditions aimed at producing fuels and lubricating oil base stocks, and the CF value of 15 is outside the scope of the current invention. Comparing the Example 7 and Example 8 results shows that the olefin selectivity at the lower CO conversion level of 12% was about twice that obtained at the higher CO conversion level of 61% (35% vs. 18%). However, Example 7 also demonstrates that while lowering CO conversion is preferred, lower CO conversion alone is not sufficient to achieve an effective level of alpha olefin production. This fact is reflected in the lower than acceptable CF in the runs of Examples 7 and 8.

What is claimed is:

1. A gas conversion process for producing linear alpha olefins having from four to twenty carbon atoms, comprising passing a synthesis gas comprising a mixture of $H_2$ and CO produced from natural gas into a linear alpha olefin hydrocarbon synthesis reactor, in which said $H_2$ and CO react in the presence of a non-shifting, Fischer-Tropsch hydrocarbon synthesis catalyst comprising a catalytic cobalt component, under reaction conditions defined by a Condition Factor (CF) greater than or equal to 50, to produce hydrocarbons, including a $C_4$–$C_{20}$ hydrocarbon fraction comprising said linear alpha olefins, wherein said condition factor is defined as:

$$CF = 200 - 0.6T + 0.03P_{H2O} - 0.6X_{CO} - 8(H_2:CO)$$

where,

T=average temperature in reactor, ° C.

$P_{H2O}$=water partial pressure in the synthesis gas feed to the linear alpha olefin reactor, kPa $X_{CO}$=% CO conversion, and $H_2$:CO=hydrogen to CO molar ratio in the synthesis gas feed to the linear alpha olefin reactor.

2. A process according to claim 1 wherein said $C_4$–$C_{20}$ hydrocarbon fraction contains less than 3 wt. % oxygenates.

3. A process according to claim 2 wherein at least 50 wt. % of said synthesized $C_4$–$C_{20}$ hydrocarbon fraction comprises said linear alpha olefins.

4. A process according to claim 3 wherein the synthesis gas passed into said linear alpha olefin hydrocarbon synthesis reactor has a $H_2$:CO mole ratio less than 2:1.

5. A process according to claim 4 wherein less than 5 mole % of said CO in said synthesis gas is converted to $CO_2$ in said reactor.

6. A process according to claim 5 wherein said $C_4$–$C_{20}$ hydrocarbon fraction contains less than 1 wt. % oxygenates.

7. A process according to claim 6 wherein at least 50 wt. % of said synthesized $C_4$–$C_{20}$ hydrocarbon fraction comprises said linear alpha olefins.

8. A process according to claim 7 wherein less than 1 mole % of said CO in said synthesis gas is converted to $CO_2$ in one pass through said reactor.

9. A gas conversion process-according to claim 8 which includes at least one hydrocarbon synthesis reactor for synthesizing hydrocarbons from synthesis gas and wherein reactor tail gas produced from said hydrocarbon synthesis reactor is utilized as feed gas for said linear alpha olefin reactor.

10. The process of claim 1 wherein said synthesis gas is treated to reduce its hydrogen concentration prior to passing into said linear alpha olefin reactor.

11. An integrated gas conversion process according to claim 10, including at least one Fischer-Tropsch hydrocarbon synthesis reactor for synthesizing hydrocarbons comprising fractions boiling in the fuel and lubricant oil ranges, from said synthesis gas which contains said $H_2$ and CO in at least a 2:1 mole ratio, wherein at least a portion of said synthesis gas is passed into said hydrocarbon synthesis reactor as the feed for said hydrocarbon synthesis.

12. A process according to claim 11 wherein said at least one linear alpha olefin and hydrocarbon synthesis reactors each produce a reactor tail gas containing unreacted $H_2$ and CO and wherein said tail gas from either or both of said at least one hydrocarbon synthesis reactor and linear alpha olefin synthesis reactors is used as feed gas alone or in combination with fresh synthesis gas to either or both of said at least one hydrocarbon synthesis reactor or linear alpha olefin reactor.

13. A process according to claim 12 wherein said $C_4$–$C_{20}$ hydrocarbon fraction synthesized in said one or more linear alpha olefin reactors has less than 1 wt. % oxygenates.

14. A process according to claim 13 wherein at least 50 wt. % of is said synthesized $C_4$–$C_{20}$ hydrocarbon fraction comprises said linear alpha olefins.

15. A process according to claim 14 wherein said at least a portion of synthesis gas passed as feed into either of said at least one hydrocarbon or linear alpha olefin synthesis reactors, is obtained by treating said synthesis gas produced from said natural gas to separate hydrogen from it and produce hydrogen and a synthesis gas having a reduced $H_2$ to CO mole ratio.

16. A process according to claim 15 wherein at least a portion of said separated hydrogen is passed into either of said at least one hydrocarbon or linear alpha olefin synthesis reactors to adjust the $H_2$ to CO mole ratio of the synthesis feed gas passed into it.

17. The process of claim 16 wherein said hydrocarbon synthesis reactor is converted into a linear alpha olefin reactor or wherein said linear alpha olefin reactor is converted into a hydrocarbon synthesis reactor by changing said reactor operating conditions but not said catalyst.

18. A process according to claim 17 wherein said $C_4$–$C_{20}$ hydrocarbon fraction contains less than 3 wt % oxygenates.

19. A process according to claim 18 wherein said $C_4$–$C_{20}$ hydrocarbon fraction contains less than 1 wt. % oxygenates and at least 50 wt. % of said linear alpha olefins.

20. A process according to claim 9 wherein products produced from said linear alpha olefin reactor and said hydrocarbon synthesis reactor are combined.

* * * * *